United States Patent
Cai et al.

(10) Patent No.: US 12,091,674 B2
(45) Date of Patent: Sep. 17, 2024

(54) LENTIVIRAL VECTOR AND METHOD FOR DELIVERING EXOGENOUS RNA BY THE LENTIVIRAL VECTOR

(71) Applicant: SHANGHAI BDGENE TECHNOLOGY CO., LTD., Shanghai (CN)

(72) Inventors: Yujia Cai, Shanghai (CN); Sikai Ling, Shanghai (CN)

(73) Assignee: SHANGHAI BDGENE TECHNOLOGY CO., LTD., Shanghai (CN)

( * ) Notice: Subject to any disclaimer, the term of this patent is extended or adjusted under 35 U.S.C. 154(b) by 891 days.

(21) Appl. No.: 17/059,415

(22) PCT Filed: Apr. 29, 2019

(86) PCT No.: PCT/CN2019/084879
§ 371 (c)(1),
(2) Date: Nov. 27, 2020

(87) PCT Pub. No.: WO2019/228117
PCT Pub. Date: Dec. 5, 2019

(65) Prior Publication Data
US 2021/0155957 A1    May 27, 2021

(30) Foreign Application Priority Data
May 29, 2018    (CN) .......................... 201810533437.X

(51) Int. Cl.
C12N 15/86    (2006.01)
A61K 48/00    (2006.01)
C12N 15/90    (2006.01)

(52) U.S. Cl.
CPC ........... *C12N 15/86* (2013.01); *C12N 15/907* (2013.01); *A61K 48/00* (2013.01); *C12N 2310/20* (2017.05); *C12N 2740/15043* (2013.01); *C12N 2740/15052* (2013.01); *C12N 2800/80* (2013.01)

(58) Field of Classification Search
None
See application file for complete search history.

(56) References Cited

U.S. PATENT DOCUMENTS

2020/0071720 A1 *   3/2020   Bouille .................. C12N 15/86

FOREIGN PATENT DOCUMENTS

WO    2007072056 A2    6/2007
WO    2017194902 A2    11/2017

OTHER PUBLICATIONS

Anne Prel et al,"Highly Efficient in Vitro and in Vivo Delivery of Functional RNAs Using New Versatile MS2-chimeric Retrovirus-like Particles" Mol Ther Methods Clin Dev., No. 2, Oct. 21, 2015 (Oct. 21, 2015), pp. 1-15.
Skrdlant, L.M., et al.,"Detection of Replication Competent Lentivirus Using a qPCR Assay for VSV-G", Mol Ther Methods Clin Dev., 2018. 8: p. 1-7.
Yujia Cai, et al., Targeted genome editing by lentiviral protein transduction of zinc-finger and TAL-effector nucleases, eLIFE, 2014, pp. 1-19, vol. 3.
Yujia Cai, et al., Lentiviral Delivery of Proteins for Genome Engineering, Current Gene Therapy, 2016, pp. 194-206, vol. 16. No. 3.

* cited by examiner

*Primary Examiner* — Celine X Qian
*Assistant Examiner* — Tiffany Nicole Grooms
(74) *Attorney, Agent, or Firm* — Bayramoglu Law Offices LLC

(57) ABSTRACT

A lentiviral vector and a method for delivering an exogenous RNA by the lentiviral vector are provided. The lentiviral vector is prepared by transfecting plasmids containing a genome sequence of the lentiviral vector into a virus-producing cell, collecting a supernatant and concentration. Specifically, according to the principle of combining an RNA-binding protein with an RNA sequence identified by the RNA-binding protein, the RNA-binding protein is integrated into a skeleton of a lentivirus GagPol long-chain protein, and the RNA sequence identified by the RNA-binding protein is connected to the exogenous target RNA, so that the exogenous target RNA is packaged into lentiviral particles during the assembly of the lentiviral particles. The exogenous target RNA can be mRNA, gRNA or RNA with other functions. The present invention can be used in the fields of gene editing, gene therapy, cell therapy, immunotherapy, regenerative medicine and basic biology.

3 Claims, 1 Drawing Sheet
Specification includes a Sequence Listing.

LENTIVIRAL VECTOR AND METHOD FOR DELIVERING EXOGENOUS RNA BY THE LENTIVIRAL VECTOR

CROSS REFERENCE TO THE RELATED APPLICATIONS

This application is the national phase entry of International Application No. PCT/CN2019/084879, filed on Apr. 29, 2019, which is based upon and claims priority to Chinese Patent Application No. 201810533437.X, filed on May 29, 2018, the entire contents of which are incorporated herein by reference.

SEQUENCE LISTING

The instant application contains a Sequence Listing which has been submitted in ASCII text format via EFS-Web and is hereby incorporated by reference in its entirety. Said text copy is named GBDD020-PKG sequence listing-20201130_ST25.txt, created on Nov. 30, 2020, and is 7244 bytes.

TECHNICAL FIELD

The present invention relates to the field of biotechnology, and in particular, to a lentiviral vector and a method for delivering an exogenous RNA by the lentiviral vector.

BACKGROUND

Lentiviral vectors are those modified from human immunodeficiency virus type 1 (HIV-1) and losing their self-replication capacity. Lentiviral vectors can efficiently infect cells and are commonly used in biological research and gene therapy. Currently, lentiviral vectors can be divided into first-generation, second-generation and third-generation. The higher the generation, the better safety.

RNA is a linear long-chain molecule formed by ribonucleotides via phosphodiester bonds. RNA can be classified into coding RNA and non-coding RNA. Coding RNAs function by encoding proteins, while non-coding RNAs do not encode proteins and can directly perform biological functions.

RNA has essential application potential in the fields of vaccine, gene therapy, gene editing and cell reprogramming. However, its application is limited by the following factors: 1) RNA is unstable and easily degraded by nuclease in the environment; (2) RNA itself cannot enter cells and requires an effective vector system; and 3) the prior RNA delivery technology is difficult to directly use in vivo.

Currently, RNA delivery methods include electroporation, chemical materials-formed nanoparticles, Sendai virus and second-generation lentiviral vectors-modified lentiviral particles. Among them, the method of second-generation lentiviral vectors-modified lentiviral particles (Prel, A., et al., Highly efficient in vitro and in vivo delivery of functional RNAs using new versatile MS2-chimeric retrovirus-like particles. Mol Ther Methods Clin Dev, 2015. 2: p. 15039.) includes the following steps of (1) integrating an MS2 coat protein (RNA-binding protein) into a lentivirus nucleocapsid (NC) protein; and (2) placing a stem-loop structure identified by the MS2 coat protein into an expression frame of a target RNA, so as to package the target RNA into the lentiviral particles. However, the second-generation lentiviral vectors retain a relatively large number of HIV genes, and the literature shows that the second-generation lentiviral vectors can generate HIV virus with replication ability in vivo (Skrdlant, L. M., et al., Detection of Replication Competent Lentivirus Using a qPCR Assay for VSV-G. Mol Ther Methods Clin Dev, 2018. 8: p. 1-7.). For the sake of safety, therefore, the second-generation lentiviral vectors are no longer used in gene therapy.

SUMMARY

The objective of the present invention is to overcome the above-mentioned problems in the prior art, and provide a lentiviral vector and a method for delivering an exogenous RNA by the lentiviral vector. The present invention solves the problem of RNA delivery into cells, including in vitro and in vivo delivery of RNA. The present invention can deliver Cas9 mRNA and gRNA for gene editing and gene therapy, can deliver tumor or virus antigen mRNA for immunotherapy, can deliver cell reprogramming factor mRNA to produce multipotent stem cells and modify cell functions, and can deliver chimeric antigen receptor mRNA for cellular immunotherapy.

The present invention packages a target RNA into a lentiviral vector, and uses the lentivirus to protect and deliver the RNA. The principle of the present invention is as follows: using an interaction between an RNA-binding protein and a stem-loop structure identified by the RNA-binding protein to package an exogenous target RNA carrying an identifiable RNA sequence into lentiviral particles.

The major features of the present invention are as follows: integrating an RNA-binding protein into an N-terminal of a third-generation lentivirus GagPol long-chain protein, and placing a stem-loop structure identified by the RNA-binding protein into an expression frame of an exogenous target RNA.

Specifically, the objective of the present invention is realized by the following technical solutions.

In the first aspect, the present invention relates to a lentiviral vector. The lentiviral vector is prepared by transfecting plasmids containing a genome sequence of the lentiviral vector into virus-producing cells, followed by collecting a supernatant and concentrating.

The genome sequence of the lentiviral vector is located on a plasmid expressing a envelope protein, a plasmid expressing a lentivirus GagPol long-chain protein containing a RNA-binding protein and a plasmid containing an RNA stem-loop structure identified by the RNA-binding protein, respectively.

Preferably, the virus-producing cells include 293T, 293FT and HEK293.

Preferably, the plasmid expressing the envelope protein includes vesicular stomatitis virus G protein (VSV-G), cluster of differentiation 4 (CD4) recognition protein, cluster of differentiation 8 (CD8) recognition protein, RD114 and baboon endogenous retrovirus envelope protein-modified envelope protein.

Preferably, the plasmid expressing the lentivirus GagPol long-chain protein containing the RNA-binding protein integrates the RNA-binding protein into an N-terminal of the third-generation lentivirus GagPol long-chain protein.

Preferably, in the plasmid expressing the lentivirus GagPol long-chain protein containing the RNA-binding protein, a codon sequence of the GagPol long-chain protein is shown in SEQ ID NO: 1.

Preferably, in the plasmid expressing the lentivirus GagPol long-chain protein containing the RNA-binding protein, the RNA-binding protein is MS2 coat protein, and a codon sequence of the MS2 coat protein is shown in SEQ ID NO: 2.

Preferably, in the plasmid containing the RNA stem-loop structure identified by the RNA-binding protein, the RNA-binding protein is MS2 coat protein, and a sequence of an RNA identified by the MS2 coat protein is shown in SEQ ID NO: 3.

Preferably, the concentrating is performed by a high-speed centrifugation or a high-performance liquid chromatography (HPLC) method.

In the second aspect, the present invention also relates to a method for delivering an exogenous target RNA by the lentiviral vector of the present invention.

Preferably, the exogenous target RNA is at least one selected from the group consisting of mRNA, gRNA and other functional RNAs.

Preferably, the method includes the following steps:
S1. co-transfecting virus-producing cells with a plasmid expressing a envelope protein, a plasmid expressing a lentivirus GagPol long-chain protein containing a RNA-binding protein and a plasmid expressing the exogenous target RNA containing an RNA stem-loop structure identified by the RNA-binding protein;
S2. collecting a supernatant containing viral particles, and concentrating to obtain lentiviral particles containing the exogenous target RNA.

Preferably, the plasmid expressing the exogenous target RNA containing the RNA stem-loop structure identified by the RNA-binding protein is obtained by fusing a sequence of an RNA identified by the RNA-binding protein with a sequence of the exogenous target RNA.

More preferably, the plasmid expressing the exogenous target RNA containing the RNA stem-loop structure identified by the RNA-binding protein is obtained by fusing a sequence of an RNA identified by MS2 coat protein with a sequence of the target RNA.

Further preferably, the sequence of the RNA identified by the MS2 coat protein is shown in SEQ ID NO: 3.

Preferably, the concentrating is performed by a high-speed centrifugation or an HPLC method.

Preferably, the virus-producing cells include 293T, 293FT and HEK293.

Preferably, the plasmid expressing the envelope protein includes VSV-G, CD4 recognition protein, CD8 recognition protein, RD114 and baboon endogenous retrovirus envelope protein-modified envelope protein.

Preferably, the plasmid expressing the lentivirus GagPol long-chain protein containing the RNA-binding protein is obtained by fusing the MS2 coat protein with the lentivirus GagPol long-chain protein.

More preferably, a codon sequence of the GagPol long-chain protein is shown in SEQ ID NO: 1; a codon sequence of the MS2 coat protein is shown in SEQ ID NO: 2.

In the third aspect, the present invention also relates to an application of the lentivirus vector of the present invention in delivering Cas9 mRNA and gRNA for gene editing and gene therapy.

In the fourth aspect, the present invention also relates to an application of the lentiviral vector of the present invention in carrying mRNAs expressing a tumor antigen and a virus antigen for vaccine.

In the fifth aspect, the present invention also relates to an application of the lentivirus vector of the present invention in expressing a cell reprogramming factor for generating multipotent stem cells and modifying cell functions.

In the sixth aspect, the present invention also relates to an application of the lentivirus vector of the present invention in delivering a chimeric antigen receptor mRNA for cellular immunotherapy.

Compared with the prior art, the present invention has the following advantages.
(1) On the basis of the third-generation lentivirus technology, HIV genes such as that and rev are removed from a lentivirus GagPol long-chain protein, which reduces the possibility of virus genome recombination producing replication-competent HIV in the process of viral particles packaging, and greatly improves the safety.
(2) The codon of the lentivirus GagPol long-chain protein is optimized, so that the lentiviral GagPol long-chain protein can be efficiently expressed in human cell lines. It is no longer necessary to express HIV protein REV to increase the production of lentiviral particles.
(3) RNA-binding protein is placed in the N-terminal of the lentivirus GagPol long-chain protein, which reduces the negative effect of exogenous protein on the normal morphology of viral particles.
(4) The present invention has the ability of packaging and carrying long-chain RNA, such as Cas9 mRNA (about 4.2 kb) and base-editing enzymes (about 5.1 kb), etc., which greatly improves the application value.
(5) The present invention can deliver Cas9 mRNA and gRNA for gene editing and gene therapy.
(6) The present invention can carry mRNAs expressing tumor antigens and virus antigens for vaccine.
(7) The present invention can be used to express cell reprogramming factors and chimeric antigen receptors for generating multipotent stem cells and modifying cell functions.

BRIEF DESCRIPTION OF THE DRAWINGS

Other features, objectives and advantages of the present invention will become more apparent upon reading the detailed description of non-restrictive embodiments with reference to the following drawings.

DETAILED DESCRIPTION OF THE EMBODIMENTS

Figure 1:
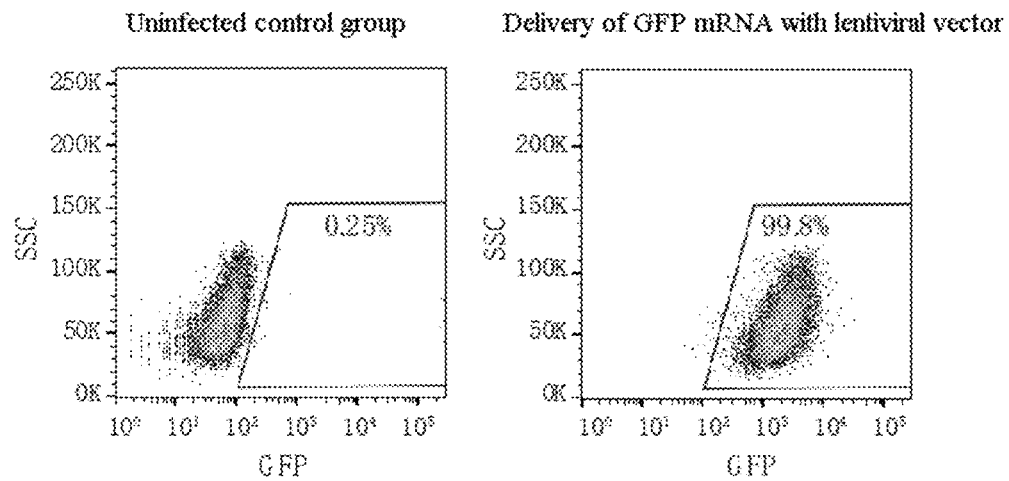
FIG. 1 is a diagram showing an experiment of a lentiviral vector delivering GFP mRNA.
Figure 2:
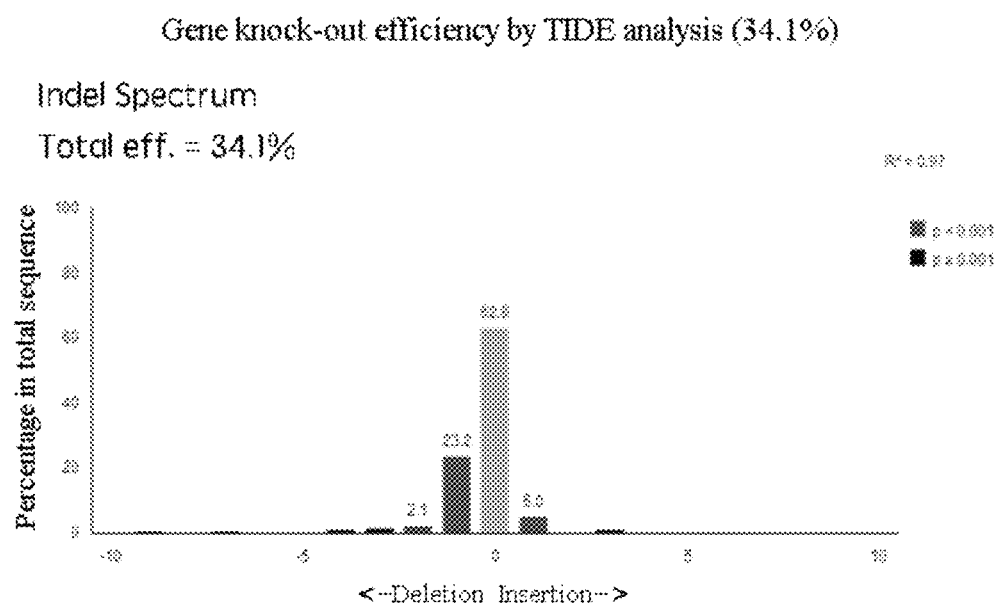
FIG. 2 is a diagram showing an experiment of a lentiviral vector delivering Cas9 mRNA for gene editing.

The present invention is described in detail below in combination with the embodiments. The following embodiments will help those skilled in the art to further understand the present invention, but will not limit the present invention in any form. It should be noted that numerous modifications and improvements may be made by those skilled in the art without departing from the spirit of the present invention. These modifications and improvements are within the protection scope of the present invention.

Embodiment 1: Preparation of Lentiviral Particles

Step 1: a plasmid expressing a envelope protein, a plasmid expressing a lentivirus GagPol long-chain protein containing a RNA-binding protein and a plasmid expressing an exogenous target RNA containing an RNA stem-loop structure identified by the RNA-binding protein are co-transfected into virus-producing cells (293T).
1) The plasmid expressing the envelope protein includes VSV-G, CD4 recognition protein, CD8 recognition protein, RD114 and baboon endogenous retrovirus envelope protein-modified envelope protein. VSV-G is selected in the present embodiment.
2) The virus-producing cells include 293T, 293FT, HEK293, etc. 293T is selected in the present embodiment.
3) The plasmid expressing the lentivirus GagPol long-chain protein containing the RNA-binding protein is obtained by fusing an MS2 coat protein with the lentivirus GagPol long-chain protein in the present embodiment.

A codon sequence of the GagPol long-chain protein is as follows (SEQ ID NO: 1):

SEQ ID NO. 1
gccagggccagcgtgctgagcggcggcgagctggacaggtgggagaagat
caggctgaggcccggcggcaagaagaagtataagctgaagcacatcgtgt
gggccagcagggagctggagaggttcgccgtgaaccccggcctgctggag
accagcgagggctgcaggcagatcctgggccagctgcagcccagcctgca
gaccggcagcgaggagctgaggagcctgtacaacaccgtggccaccctgt
actgcgtgcaccagaggatcgagatcaaggacaccaaggaggccctggac
aagatcgaggaggagcagaacaagtccaagaagaaggcccagcaggccgc
cgccgacaccggccacagcagccaggtgagccagaactaccccatcgtgc
agaacatccagggccagatggtgcaccaggccatcagccccaggaccctg
aacgcctgggtgaaggtggtggaggagaaggccttcagcccgaggtgat
ccccatgttcagcgccctgagcgagggagccaccccccaggacctgaaca
ccatgctgaacaccgtgggcggccaccaggccgccatgcagatgctgaag
gagaccatcaacgaggaggccgccgagtgggacagggtgcaccccgtgca
cgccggccccatcgcccccggccagatgagggagccccgcggcagcgaca
tcgccggcaccaccagcaccctgcaggagcagatcggctggatgaccaac
aaccccccatccccgtgggcgaaatctacaagaggtggatcatcctggg
cctgaacaagatcgtgaggatgtacagccccaccagcatcctggatatca
ggcagggccccaaagagcccttcagggactacgtggacaggttctacaag
accctgcgcgccgagcaggccagccaggaggtgaagaactggatgaccga
gaccctgctggtgcagaacgccaaccccgactgcaagaccatcctgaagg
ccctgggacccgccgccaccctggaggagatgatgaccgcctgccagggc
gtgggcggccccggccacaaggccagggtgctggccgaggccatgagcca
ggtgaccaacaccgccaccatcatgatgcagaggggcaacttcaggaacc
agaggaagatggtgaagtgcttcaactgcggcaaggaggccacaccgcc
aggaactgccgcgcccccaggaagaagggctgctggaagtgcggcaagga
gggccaccagatgaaggactgcaccgagaggcaggctaatttttttaggga
agatctggccttcctcaaagggaaggccagggaattttcttcagagcaga
ccagagccaacagccccaccatttcttcagagcagaccagagccaacagc -continued cccaccagaagagagcttcaggtctggggtagagacaacaactcccctc
agaagcaggagccgatagacaaggaactgtatcctttaacttccctcaga
tcactctttggcaacgacccctcgtcacaataaagatcggtggccagctg
aaggagggccctgctggacaccggcgccgacgacaccgtgctggaggagat
gagcctgccccggcaggtggaagcccaagatgatcggcggcatcggcggct
tcatcaaggtgaggcagtacgaccagatcctgatcgagatctgcggccac
aaggccatcggcaccgtgctggtgggaccctacacctgtgaacatcatcgg
caggaacctgctgacccagatcggctgcaccctgaacttccccatcagcc
ccatcgagaccgtgcccgtgaagctgaagcccggcatggacggccctaag
gtgaagcagtggccctgaccgaggagaagatcaaggccctggtggagat
ctgcaccgagatggagaaggagggcaagatcagcaagatcggcccgaga
acccctacaacacccccgtgttcgccatcaagaagaaggacagcaccaag
tggaggaagctggtggacttcagggagctgaacaagaggacccaggactt
ctgggaggtgcagctgggcatccccacccgccggcctgaagaagaaga
agagcgtgaccgtgctggacgtgggcgacgcctacttcagcgtgcccctg
gacgaggacttcaggaagtataccgccttcaccatccccagcatcaacaa
cgagaccccggcatccgctaccagtacaacgtgctgcccaggctgga
agggcagccccgccatcttccagagcagcatgacaaagatcctggagccc
ttcaagaagcagaaccccgacatcgtgatctatcagtacatggacgacct
gtacgtgggcagcgacctggagatcggccagcacaggaccaagatcgagg
agctgaggcagcacctgctgaggtggggcctgaccaccccccgacaagaag
caccagaaggagcccccattcctgtggatgggctacgagctgcacccga
caagtggaccgtgcagcccatcgtgctgcccgagaaggacagctggaccg
tgaacgacattcagaagctggtgggcaagctgaactgggccagccagatc
taccccggcatcaaggtgaggcagctgtgcaagctgctgagggcacaaa
ggctctgaccgaggtgatccccctgaccgaggaggccgagctggagctgg
ccgagaacagggagatcctgaaggagcccgtgcacggcgtgtactacgac
cccagcaaggacctgatcgccgagatccagaagcagggccagggccagtg
gacctaccagatctaccaggagccttcaagaacctgaagaccggcaagt
acgcccgcatgcgcggcgcccacaccaacgacgtgaagcagctgaccgag
gccgtgcagaagatcaccaccgagagcatcgtgatctggggcaagactcc
taagttcaagctgcccatccagaaggagacctgggagacctggtggaccg
agtactggcaggccacctggattcccgagtgggagttcgtgaacaccccct
cccctggtgaagctgtggtatcagctggagaaggagcccatcgtgggcgc
cgagaccttctacgtggacggcgccgccaacagggagaccaagctgggca
aggccggctacgtgaccaacaagggccgccagaaggtggtgcccctgacc
aacaccaccaaccagaagaccgagctgcaggctatctacctggccctgca
ggactcaggcctggaggtaacatcgtgaccgacagccagtacgccctgg
gcatcatccaggcccagcccgacaagagcgagagcgagctggtgaaccag
atcatcgagcagctgatcaagaaggagaaggtgtacctggcctgggtgcc
cgcccacaagggcatcggcggcaacgagcaggtggacaagctggtgagcg -continued ccggcatcaggaagatcctgttcctggacggcatcgacaaggcccaggac gagcacgagaagtaccacagcaactggagggctatgctagcgacttcaa cctgcctcccgtggtggctaaggagatcgtggccagctgcgacaagtgcc agctgaagggcgaggccatgcacggccaggtggactgcagccccggcatc tggcagctggtttgcacccacctggagggcaaggtgatcctggtggccgt gcacgtggcctccggctacatcgaggccgaggtgatccccgccgagaccg gccaggagaccgcctacttcctgctgaagctggccggccgctggcccgtg aagaccatccacaccgacaacggcagcaacttcaccagcgccaccgtgaa ggccgcctgctggtgggccggcatcaagcaggagttcggcatcccctaca accccagtctcagggcgtggtggagagcatgaacaaggagctgaagaag atcatcggccaggtgagggaccaggccgagcacctgaagaccgccgtgca gatggccgtgttcatccacaacttcaagaggaagggcggcatcggcggct acagcgccggcgagaggatcgtggacatcatcgccaccgacatccagacc aaggagctgcagaagcagatcaccaagatccagaacttcaggggtgtacta cagggacagcaggaaccctctgtggaagggccccgccaagctgctgtgga agggcgagggcgccgtggtgatccaggacaacagcgacatcaaggtggtg cccaggaggaaggccaagatcatcagggactacggcaagcagatggccgg cgacgactgcgtggcctccaggcaggacgaggactga.

accagagccaacagccccaccatttcttcagagcagaccagagccaacagccc
caccagaagagagcttcaggtctggggtagaga
caacaactcccccctcagaagcaggagccgatagacaaggaactgtatcctt
taacttccctcagatcactctttggcaacgacccctcgt cacaataaa
gatcggtggccagct-
gaaggaggccctgctggacaccggcgccgacgacaccgtgctggaggag
atgagcctgccc ggcaggtggaagcccaagatgatcggcggcatcggcggctt
catcaaggtgaggcagtacgaccagatcctgatcgagatctgcgg
ccacaaggccatcggcaccgtgctggtgggacctacacctgtgaacat
catcggcaggaacctgctgacccagatcggctgcaccct gaacttccc
catcagccccatcgagaccgtgcccgtgaagctgaagcccgg
catggacggccctaaggtgaagcagtggcccctga
ccgaggagaagatcaaggccctggtggagatctgcaccgagatg
gagaaggagggcaagatcagcaagatcggccccgagaacc ccta
caacaccccgtgttcgccatcaagaagaaggacagcaccaagtggag
gaagctggtggacttcagggagctgaacaagag
gacccaggacttctggaggtgcagctgggcatcccccaccccgccggcct
gaagaagaagaagagcgtgaccgtgctggacgtg ggcgacgcc
tacttcagcgtgccctggacgaggacttcaggaagtataccgccttcac
catcccagcatcaacaacgagaccccc
ggcatccgctaccagtacaacgtgctgccccagggctggaagggcagccccgc
catcttccagagcagcatgacaaagatcctgga gccctt
caagaagcagaaccccgacatcgtgatctatcagta
catggacgacctgtacgtgggcagcgacctggagatcggccagca
caggaccaagatcgaggagctgaggcagcacctgctgaggtggggcctgac
cacccccgacaagaagcaccagaaggagcccc cattcctgtggatgggc
tacgagctgcaccccgacaagtggaccgtgcagcc
catcgtgctgcccgagaaggacagctggaccgtg
aacgacattcagaagctggtggccaagctgaactgggccagccagatc
taccccggcatcaaggtgaggcagctgtgcaagctgct
gaggggcacaaaggctctgaccgaggtgatcccctgaccgag
gaggccgagctggagctggccgagaacagggagatcctgaa
ggagcccgtgcacggcgtgtactacgaccccagcaaggacct
gatcgccgagatccagaagcagggccagggccagtggaccta ccagatc
taccaggagcccttcaagaacctgaagaccggcaagtacgcccg
catgcgcggcgcgcccacaccaacgacgtgaagcag ctgaccgaggccgtgcagaagatcaccaccgagagcatcgtgatctggggcaa
gactcctaagttcaagctgcccatccagaagga gacctggga
gacctggtggaccgagtactggcaggccacctggattcccgagtgggagttcgt
gaacacccctcccctggtgaagct
gtggtatcagctggagaaggagcccatcgtgggcgccgagaccttc
tacgtggacggcgccgccaacagggagaccaagctgggc aaggccggc
tacgtgaccaacaaggggccgccagaaggtggtgcccctgaccaacaccac
caaccagaagaccgagctgcaggct
atctacctggccctgcaggactcaggcctggaggtgaa
catcgtgaccgacagccagtacgccctgggcatcatccaggcccagcc
cgacaagagcgagagcgagctggtgaaccagatcatcgagcagctgat
caagaaggagaaggtgtacctggcctgggtgccccgcc cacaaggg
catcggcggcaacgagcaggtggacaagctggtgagcgccggcatcaggaa
gatcctgttcctggacggcatcgaca
aggcccaggacgagcacgagaagtaccacagcaactggagggc
tatgctagcgacttcaacctgcctcccgtggtggctaaggag
atcgtggccagctgcgacaagtgccagctgaagggcgaggc
catgcacggccaggtggactgcagccccggcatctggcagctgg tttgcacc
cacctggagggcaaggtgatcctggtggccgtgcacgtggcctccggcta
catcgaggccgaggtgatccccgccgag
accggccaggagaccgcctacttcctgctgaagctggccggccgctggcccgt
gaagaccatccacaccgacaacggcagcaactt caccagcgccaccgt
gaaggccgcctgctggtgggccggcatcaagcaggagttcggcatcccta
caaccccagtctcagggc
gtggtggagagcatgaacaaggagctgaagaagatcatcggccaggt
gagggaccaggccgagcacctgaagaccgccgtgcag atggccgtgttcatc
cacaacttcaagaggaagggcggcatcggcggctacagcgccggcgagag
gatcgtggacatcatcgccac
cgacatccagaccaaggagctgcagaagcagatcaccaa
gatccagaacttcaggggtgtactacagggacagcaggaaccctctgt
ggaagggccccgccaagctgctgtggaagggcgagggcgccgtggt
gatccaggacaacagcgacatcaaggtggtgcccagga ggaaggccaagat
catcagggactacggcaagca
gatggccggcgacgactgcgtggcctccaggcaggacgaggactga SEQ ID NO: 1.

A codon sequence of the MS2 coat protein is as follows (SEQ ID NO: 2), and its encoded protein can be linked to the GagPol long-chain protein encoded by the sequence of SEQ ID NO: 1, for example, the protein encoded by the MS2 coat protein is placed on the N-terminal of the GagPol long-chain protein.

SEQ ID NO. 2
atggcctctaattttactcaatttgtgcttgtcgataatgggggacggg agatgtgaccgttgcccctagcaatttcgcaaatggcgttgcagaatgga tctctagcaacagcagaagccaagcgtacaaagtaacgtgttccgttcgc caaagctccgcccaaaaacggaagtatacaataaaggttgaggtgccgaa agtagccactcaaacagttggtggggtagaattgcccgtagcggcatggc ggtcatatctcaatatggaactcactatcccaatcttcgccacgaatagc gattgtgagctgatagttaaggctatgcaaggtcttctcaaagatggaaa ccctattccatctgctatcgccgccaacagcgggatatac.

4) The plasmid expressing the exogenous target RNA containing the RNA stem-loop structure identified by the RNA-binding protein is obtained by fusing a sequence of an RNA identified by the MS2 coat protein with a sequence of the target RNA.

The sequence of the RNA identified by the MS2 coat protein is as follows (SEQ ID NO: 3), which can be linked with the exogenous target RNA by single or multiple repeats.

SEQ ID No. 3
ACAUGAGGAUCACCCAUGU.

5) The plasmids for preparing lentiviral particles carrying the exogenous target RNA mentioned in 3) and 4) above are obtained by a molecular cloning method.

Step 2: a supernatant containing viral particles is collected and concentrated by a high-speed centrifugation or a HPLC method to obtain the lentiviral particles containing the exogenous target RNA with a high titer.

Embodiment 2: Delivery of GFP mRNA Using a Lentiviral Vector

The specific steps are the same as those in embodiment 1. GFP mRNA is selected as an exogenous target RNA. Green fluorescent protein (GFP) is a fluorescent protein as a reporter gene. The present embodiment specifically delivers the GFP mRNA into 293T cells by a lentiviral vector.

As shown in FIG. 1, after the 293T cells are infected with lentiviral particles carrying the GFP mRNA for 48 h, GFP positive cells reached 99.8% by flow cytometry.

Embodiment 3: Delivery of Cas9 mRNA and gRNA Targeting AAVS1 Site by a Lentiviral Vector The specific steps are the same as those in embodiment 1. Cas9 mRNA and gRNA targeting AAVS1 site are selected as exogenous target RNAs. The present embodiment specifically delivers the Cas9 mRNA and the gRNA targeting the AAVS1 site of human

What is claimed is:

1. A lentiviral vector, wherein the lentiviral vector is prepared by transfecting plasmids containing a genome sequence of the lentiviral vector into a virus-producing cell, collecting a first supernatant and concentrating the first supernatant;
- the plasmids comprise a plasmid expressing an envelope protein, a plasmid expressing a lentivirus GagPol long-chain protein containing an RNA-binding protein and a plasmid containing exogenous target RNA with an RNA stem-loop structure identified by the RNA-binding protein;
- wherein the plasmid expressing the lentivirus GagPol long-chain protein containing the RNA-binding protein integrates the RNA-binding protein into an N-terminal of a third-generation lentivirus GagPol long-chain protein, and the plasmid expressing the envelope protein is VSV-G;
- wherein a codon sequence of the lentivirus GagPol long-chain protein is SEQ ID NO: 1; and
- wherein the RNA-binding protein is MS2 coat protein, and a codon sequence of the MS2 coat protein is SEQ ID NO: 2.

2. The lentiviral vector according to claim 1, wherein in the plasmid containing the RNA stem-loop structure, the RNA stem-loop structure is an RNA sequence identified and bound by the RNA-binding protein, and wherein the RNA sequence is SEQ ID NO: 3.

3. The method according to claim 1, wherein the virus-producing cell is one selected from the group consisting of 293T, 293FT and HEK293.

* * * * *

SEQUENCE LISTING

```
<160> NUMBER OF SEQ ID NOS: 3

<210> SEQ ID NO 1
<211> LENGTH: 4337
<212> TYPE: DNA
<213> ORGANISM: Artificial Sequence
<220> FEATURE:
<223> OTHER INFORMATION: The sequence is synthetized.
<220> FEATURE:
<221> NAME/KEY: misc_feature
<223> OTHER INFORMATION: codon sequence of GagPol long-chain protein

<400> SEQUENCE: 1
gccagggcca gcgtgctgag cggcggcgag ctggacaggt gggagaagat caggctgagg        60
cccggcggca agaagaagta taagctgaag cacatcgtgt gggccagcag ggagctggag       120
aggttcgccg tgaacccgg cctgctggag accagcgagg gctgcaggca gatcctgggc       180
cagctgcagc ccagcctgca gaccggcagc gaggagctga ggagcctgta caacaccgtg       240
gccaccctgt actgcgtgca ccagaggatc gagatcaagg acaccaagga ggccctggac       300
aagatcgagg aggagcagaa caagtccaag aagaaggccc agcaggccgc cgccgacacc       360
ggccacagca gccaggtgag ccagaactac cccatcgtgc agaacatcca gggccagatg       420
gtgcaccagg ccatcagccc caggaccctg aacgcctggg tgaaggtggt ggaggagaag       480
gccttcagcc ccgaggtgat ccccatgttc agcgccctga gcgagggagc caccccccag       540
gacctgaaca ccatgctgaa caccgtgggc ggccaccagg ccgccatgca gatgctgaag       600
gagaccatca acgaggaggc cgccgagtgg acagggtgc accccgtgca cgccggcccc       660
atcgcccccg gccagatgag ggagcccgc ggcagcgaca tcgccggcac caccagcacc       720
ctgcaggagc agatcggctg gatgaccaac aacccccca tccccgtggg cgaaatctac       780
aagaggtgga tcatcctggg cctgaacaag atcgtgagga tgtacagccc caccagcatc       840
ctggatatca ggcagggccc caaagagccc ttcagggact acgtggacag gttctacaag       900
accctgcgcg ccgagcaggc cagccaggag gtgaagaact ggatgaccga gaccctgctg       960
gtgcagaacg ccaaccccga ctgcaagacc atcctgaagg ccctgggacc cgccgccacc      1020
ctggaggaga tgatgaccgc ctgccagggc gtgggcggcc ccgccacaa ggccagggtg      1080 ctggccgagg ccatgagcca ggtgaccaac accgccacca tcatgatgca gaggggcaac      1140
```

```
ttcaggaacc agaggaagat ggtgaagtgc ttcaactgcg gcaaggaggg ccacaccgcc   1200
aggaactgcc gcgccccccag gaagaagggc tgctggaagt gcggcaagga gggccaccag   1260
atgaaggact gcaccgagag gcaggctaat tttttaggga agatctggcc ttcctacaag   1320
ggaaggccag ggaattttct tcagagcaga ccagagccaa cagccccacc atttcttcag   1380
agcagaccag agccaacagc cccaccagaa gagagcttca ggtctggggt agagacaaca   1440
actccccctc agaagcagga gccgatagac aaggaactgt atcctttaac ttccctcaga   1500
tcactctttg gcaacgaccc ctcgtcacaa taaagatcgg tggccagctg aaggaggccc   1560
tgctggacac cggcgccgac gacaccgtgc tggaggagat gagcctgccc ggcaggtgga   1620
agcccaagat gatcggcggc atcggcggct tcatcaaggt gaggcagtac gaccagatcc   1680
tgatcgagat ctgcggccac aaggccatcg gcaccgtgct ggtgggacct acacctgtga   1740
acatcatcgg caggaacctg ctgacccaga tcggctgcac cctgaacttc cccatcagcc   1800
ccatcgagac cgtgcccgtg aagctgaagc ccggcatgga cggccctaag gtgaagcagt   1860
ggcccctgac cgaggagaag atcaaggccc tggtggagat ctgcaccgag atggagaagg   1920
agggcaagat cagcaagatc ggccccgaga accccctacaa caccccgtg ttcgccatca   1980
agaagaagga cagcaccaag tggaggaagc tggtggactt cagggagctg aacaagagga   2040
cccaggactt ctgggaggtg cagctgggca tcccccaccc cgccggcctg aagaagaaga   2100
agagcgtgac cgtgctggac gtgggcgacg cctacttcag cgtgcccctg gacgaggact   2160
tcaggaagta ccgccttc accatcccca gcatcaacaa cgagacccc ggcatccgct   2220
accagtacaa cgtgctgccc cagggctgga agggcagccc cgccatcttc cagagcagca   2280
tgacaaagat cctggagccc ttcaagaagc agaaccccga catcgtgatc tatcagtaca   2340
tggacgacct gtacgtgggc agcgacctgg agatcggcca gcacaggacc aagatcgagg   2400
agctgaggca gcacctgctg aggtggggcc tgaccacccc cgacaagaag caccagaagg   2460
agcccccatt cctgtggatg ggctacgagc tgcacccccga caagtggacc gtgcagccca   2520
tcgtgctgcc cgagaaggac agctggaccg tgaacgacat tcagaagctg gtgggcaagc   2580
tgaactgggc cagccagatc tacccccggca tcaaggtgag gcagctgtgc aagctgctga   2640
ggggcacaaa ggctctgacc gaggtgatcc ccctgaccga ggaggccgag ctggagctgg   2700
ccgagaacag ggagatcctg aaggagcccg tgcacgcgt gtactacgac cccagcaagg   2760
acctgatcgc cgagatccag aagcagggcc agggccagtg gacctaccag atctaccagg   2820
agcccttcaa gaacctgaag accggcaagt acgcccgcat gcgcggcgcc cacaccaacg   2880
acgtgaagca gctgaccgag gccgtgcaga agatcaccac cgagagcatc gtgatctggg   2940
gcaagactcc taagttcaag ctgcccatcc agaaggagac ctgggagacc tggtggaccg   3000
agtactggca ggccacctgg attcccgagt gggagttcgt gaacacccct cccctggtga   3060
agctgtggta tcagctggag aaggagccca tcgtgggcgc cgagaccttc tacgtggacg   3120
gcgccgccaa cagggagacc aagctgggca aggccggcta cgtgaccaac aagggccgcc   3180
agaaggtggt gcccctgacc aacaccacca ccagaagac cgagctgcag gctatctacc   3240
tggccctgca ggactcaggc ctggaggtga acatcgtgac cgacagccag tacgccctgg   3300
gcatcatcca ggcccagccc gacaagagcg agagcgagct ggtgaaccag atcatcgagc   3360
agctgatcaa gaaggagaag gtgtacctgg cctgggtgcc cgcccacaag ggcatcggcg   3420
gcaacgagca ggtggacaag ctggtgagcg ccggcatcag gaagatcctg ttcctggacg   3480
```

```
gcatcgacaa ggcccaggac gagcacgaga agtaccacag caactggagg gctatggcta    3540
gcgacttcaa cctgcctccc gtggtggcta aggagatcgt ggccagctgc gacaagtgcc    3600
agctgaaggg cgaggccatg cacgccaggt ggactgcag ccccggcatc tggcagctgg     3660
tttgcaccca cctggagggc aaggtgatcc tggtggccgt gcacgtggcc tccggctaca    3720
tcgaggccga ggtgatcccc gccgagaccg gccaggagac cgcctacttc ctgctgaagc    3780
tggccggccg ctggcccgtg aagaccatcc acaccgacaa cggcagcaac ttcaccagcg    3840
ccaccgtgaa ggccgcctgc tggtgggccg gcatcaagca ggagttcggc atcccctaca    3900 accccagtc tcagggcgtg gtggagagca tgaacaagga gctgaagaag atcatcggcc     3960
aggtgaggga ccaggccgag cacctgaaga ccgccgtgca gatggccgtg ttcatccaca    4020
acttcaagag gaagggcggc atcggcggct acagcgccgg cgagaggatc gtggacatca    4080
tcgccaccga catccagacc aaggagctgc agaagcagat caccaagatc cagaacttca    4140
gggtgtacta cagggacagc aggaaccctc tgtggaaggg ccccgccaag ctgctgtgga    4200
agggcgaggg cgccgtggtg atccaggaca acagcgacat caaggtggtg cccaggagga    4260
aggccaagat catcagggac tacggcaagc agatggccgg cgacgactgc gtggcctcca    4320
ggcaggacga ggactga                                                  4337

<210> SEQ ID NO 2
<211> LENGTH: 390
<212> TYPE: DNA
<213> ORGANISM: Bacteriophage MS2
<220> FEATURE:
<221> NAME/KEY: misc_feature
<223> OTHER INFORMATION: codon sequence of MS2 coat protein

<400> SEQUENCE: 2
atggcctcta attttactca atttgtgctt gtcgataatg gggggacggg agatgtgacc     60 gttgcccta gcaatttcgc aaatggcgtt gcagaatgga tctctagcaa cagcagaagc    120
caagcgtaca agtaacgtg ttccgttcgc caaagctccg cccaaaaacg aagtataca     180 ataaaggttg aggtgccgaa agtagccact caaacagttg gtgggtaga attgcccgta    240 gcggcatggc ggtcatatct caatatggaa ctcactatcc caatcttcgc cacgaatagc    300
gattgtgagc tgatagttaa ggctatgcaa ggtcttctca agatggaaa ccctattcca    360 tctgctatcg ccgccaacag cgggatatac                                    390

<210> SEQ ID NO 3
<211> LENGTH: 19
<212> TYPE: RNA
<213> ORGANISM: Artificial Sequence
<220> FEATURE:
<223> OTHER INFORMATION: The sequence is synthetized.
<220> FEATURE:
<221> NAME/KEY: misc_feature
<223> OTHER INFORMATION: sequence of RNA identified by the MS2 coat
      protein

<400> SEQUENCE: 3
acaugaggau cacccaugu                                                 19
```